United States Patent [19]
Meredith et al.

[11] Patent Number: 6,063,336
[45] Date of Patent: *May 16, 2000

[54] METHOD AND APPARATUS FOR WOOD CHIP PASTEURIZATION

[75] Inventors: Michael D. Meredith, Tigard, Oreg.; Garth L. Tomic, Vancouver, Wash.

[73] Assignee: Westward Corporation, Eugene, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/691,324

[22] Filed: Aug. 2, 1996

[51] Int. Cl.⁷ .............................. A61L 2/04; B63B 19/18
[52] U.S. Cl. .............................. 422/38; 422/40; 422/307; 114/202
[58] Field of Search .............................. 422/1, 26, 40, 422/292, 307, 309, 38, 39; 162/187, 233, 249, 250; 426/521, 399, 401; 99/483; 114/73, 117, 120, 174, 202, 201 A

[56] References Cited

U.S. PATENT DOCUMENTS

| | | | |
|---|---|---|---|
| 84,733 | 8/1868 | Cowling | 422/39 X |
| 399,196 | 3/1889 | Haskin | 422/39 X |
| 1,672,326 | 6/1928 | Kobiolke | 422/39 X |
| 3,612,303 | 10/1971 | Ikeda | 114/202 |
| 3,837,271 | 9/1974 | Shore et al. | 422/38 X |
| 3,949,099 | 4/1976 | Kaufman | 426/521 |
| 3,959,529 | 5/1976 | Winn et al. | 422/39 X |
| 4,237,809 | 12/1980 | Hickmann | 114/202 |
| 4,284,120 | 8/1981 | Gloersen . | |
| 4,304,224 | 12/1981 | Fortney | 422/120 X |
| 4,921,719 | 5/1990 | Kohlbach | 426/521 |
| 5,447,686 | 9/1995 | Seidner | 422/26 |

*Primary Examiner*—Elizabeth McKane
*Attorney, Agent, or Firm*—William A. Birdwell & Associates

[57] ABSTRACT

A method and apparatus for pasteurizing comminuted wood. A housing is substantially sealed over the hatch of a ship's cargo hold before it is opened. The hold contains comminuted wood for transport, which are typically contaminated with pathogens that it is desired to destroy. Hot water is provided to combine with the comminuted wood to form a slurry. The slurry is pumped to a pasteurization vessel where it is held for a predetermined pasteurization temperature and time. Subsequent to the predetermined pasteurization time, the slurry exits the pasteurization vessel and the water is reclaimed from the wood chips. The reclaimed water is preferentially reused to slurry more chips. The method and apparatus preferably include employing an air removal and cleaning system which maintains the environment within the cargo hold at conditions tolerable for a worker to work therein, the air removal and cleaning system purifying the air obtained therefrom before exhausting it into the atmosphere.

21 Claims, 1 Drawing Sheet

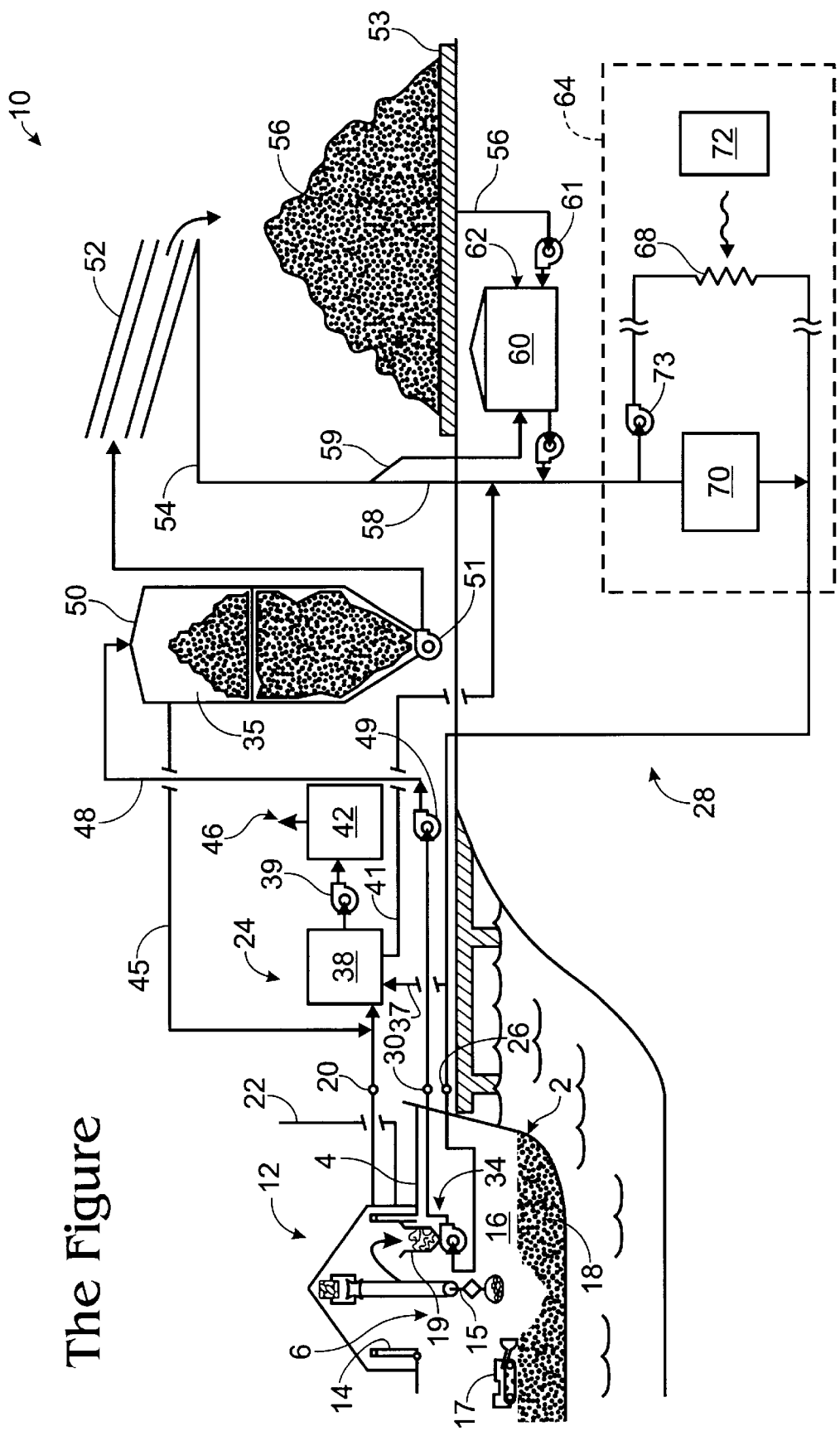
The Figure

METHOD AND APPARATUS FOR WOOD CHIP PASTEURIZATION

BACKGROUND OF THE INVENTION

This invention relates to methods and apparatus for ridding wood chips, particularly imported wood chips, of pathogens such as insects, nematodes and fungi. More particularly, the invention pertains to such methods and apparatus employing hot water for pasteurization and for transport of the wood chips from a vessel, for example a ship, and an air circulation system to prevent escapement of pathogens.

Imported wood fiber of any sort and imported wood chips in particular, hereinafter referred to as "comminuted wood," pose a health threat to domestic plant species in potentially carrying pathogens from a site of origin to a site of delivery. Typically, poisonous chemicals such as aluminum phosphide or methyl bromide have been used for fumigation of imported wood fiber such as wood chips. However, such treatment chemicals cannot penetrate wood chips or large containers adequately within reasonable time. In addition, poisons are expensive to apply and must be handled and disposed of with utmost care. In addition, methyl bromide has been implicated by the Environmental Protection Agency in contributing to ozone depletion and its use is controversial. There is, generally, a conflict between the ability of a poison to function and to be harmless to the natural environment.

Attempts to employ a non-toxic and environmentally compatible agent for exterminating insects include utilizing an inert freezing liquid, such as liquid nitrogen, as proposed for example in Tallon, U.S. Pat. No. 5,165,199. However, the method of Tallon is employed for relatively small areas and volumes, as liquid nitrogen can be prohibitively expensive in large quantities. Moreover, liquid nitrogen must generally be kept away from structures or articles that it is desired should not become brittle in view of stresses placed thereon. In addition, a freezing agent may not be effective against some pathogens, such as eggs, spores and seeds.

Pasteurization has long been used to treat food products, particularly milk products, and it has even been proposed in Roth et al., U.S. Pat. No. 5,372,149 to pasteurize snuff. In the particular process of Roth, it is proposed to cook snuff in a steam jacketed vessel with stirring plows to bring the snuff into contact with the heated walls.

While pasteurization has been employed in articles for human ingestion, it has apparently not been proposed to employ such a process in the treatment of wood chips. In particular, it has not been previously known how to apply such a process in the treatment of imported wood chips, which are generally delivered to a delivery site in extremely large quantities in a ship's cargo hold, where it is desirable to prevent the escape of pathogens to the local environment.

Accordingly, there is a need for a novel and improved method and apparatus for wood chip pasteurization that pasteurizes wood chips prior to exposure to the local atmosphere and which is relatively inexpensive, non-toxic and environmentally compatible.

SUMMARY OF THE INVENTION

The method and apparatus for pasteurizing wood chips of the present invention solves the aforementioned problems and meets the aforementioned needs by employing a housing which is set upon and substantially seals the hatch of a ship's cargo hold in which wood chips are held, the housing being connected to an air removal and cleaning system, and employing an inlet to the hold for hot water and an outlet for a slurry, the slurry being a combination of the wood chips and the hot water.

The air removal and cleaning system controls the temperature within the ship's hold and provides fresh air so that a person may work therein to deliver the wood chips to the slurry conveying system. Preferably as well, the air removal and cleaning system maintains a slightly negative air pressure within the housing which, along with the seal, helps to prevent pathogens from escaping into the atmosphere.

The hot water outlet of the hot water system is fed into the inlet of the slurry conveying system into which wood chips are also fed by the human operator aided by a machine, e.g., a clam-shell or bucket, to create the slurry. The slurry is pumped through a sealed pipe feeding a remotely located pasteurization vessel wherein the slurry is deposited at the top and is pumped from the bottom. The slurry is caused to be held in the vessel at a predetermined minimum pasteurization temperature, determined by the hot water temperature, for a predetermined minimum pasteurization time. Subsequently, the slurry is pumped from the pasteurization vessel and drained, and the remaining wood chips are output from the system for collection and transport.

Water drained from the slurry is collected, reheated as necessary to reach the temperature required for the process, and recirculated to produce the slurry. Waste heat may be used to reheat the water.

Therefore, it is a principal object of the present invention to provide a novel method and apparatus for pasteurizing wood chips.

It is another object of the present invention to provide such a method and apparatus that isolates wood chips from the local atmosphere and pasteurizes the wood chips before exposure to the local atmosphere.

It is still another object of the present invention to provide such a method and apparatus that is relatively inexpensive.

It is a further object of the present invention to provide such a method and apparatus that does not rely on toxic substances.

It is still a further object of the present invention to provide such a method and apparatus that is environmentally compatible.

The foregoing and other objects, features and advantages of the present invention will be more readily understood upon consideration of the following detailed description of the invention, taken in conjunction with the following drawing.

BRIEF DESCRIPTION OF THE DRAWING

The FIGURE is a schematic of a method and apparatus for pasteurizing wood chips according to the present invention.

DETAILED DESCRIPTION OF A PREFERRED EMBODIMENT

Referring to the Figure, a method and apparatus ("the system") for pasteurizing wood chips 10 is shown. The system pertains to pasteurizing wood chips that are held in the cargo hold 16 of a sea-going vessel 2. The vessel 2 has an upper decking surface 4 which has an opening 6 therethrough for accessing the cargo hold. Around the opening 6 is a hatch 14 which covers and protects the opening 6 and is adapted to open upwardly (as shown).

The wood chips are held in the cargo hold to prevent the escape of pathogens to the external atmosphere. However, when opening the hatch at the port of entry of the vessel, the chips normally become exposed to the local atmosphere. To prevent this, a housing 12 is provided for removable placement over the opening 6 and the hatch 14. Preferably, the housing is placed over the hatch at the site of delivery of the wood chips before opening the hatch, so that the wood chips may be rid of pathogens before being exposed to the local atmosphere.

The housing sits on the upper decking surface 4 as shown in the Figure. The housing is large enough to permit the hatch 14 its full range of opening when the housing is set thereover, and to provide room for workers and machinery, such as cranes and bulldozers, to fit inside and operate on the comminuted wood, to unload the wood from the vessel and treat it on shore as described more fully below.

During shipping, micro-organisms acting on the wood chips 18 typically create an oxygen poor environment within the hold 16, in which the temperature is typically about 140 degrees Fahrenheit and the humidity is nearly 100 percent. It is desirable to neutralize this hostile environment to permit the workers to work within the housing and the hold. For this purpose, the housing is adapted for sealing around the hatch 14, through contact with the upper decking surface 4, to prevent the escape of pathogens from the hold.

In support of this purpose an air removal and cleaning system 24 is provided. The housing 12 is connected to the air removal and cleaning system at output manifold 20. A filter 42 is provided for removing entrained organisms and particulates from the air. Fan 39 transfers the air through the filter 42. The air passing through the filter is then expelled into the atmosphere through an atmospheric air outlet 46.

In addition, air removed from the hold 16 through the manifold 20 may be treated with water to remove a large portion of the particulates prior to filtering. Hot water may be employed to pasteurize the airborne particulates. The air is transferred through a hot scrubber 38 to the filter 42, the hot scrubber contacting hot water with the air. Hot water is provided at inlet 37 and expelled at outlet 41 as described below.

The air removal and cleaning system 24 maintains a slightly negative air pressure in the hold 16 to prevent the escape of pathogens into the atmosphere. The air removal and cleaning system 24 preferably also receives air from a pasteurizing vessel 50 via conduit 45 for cleaning air within that vessel. Although adequate fresh air for personnel working within the vessel would ordinarily leak into the vessel due to the negative pressure therein, an air inlet 22 may be provided to supply fresh air.

The hopper 19 is connected to an input manifold 26 of a hot water circulation system 28, the hot water being circulated through the hopper 19 and being output at a manifold 30 of the hot water circulation system 28.

The wood chips 18 are fed into the hopper 19 of the hot water circulation system 28 by an appropriate means, such as a bulldozer 17 and crane 15. The wood chips 18 combine with the hot water provided by the hot water circulation system 28 to form the slurry 34.

The slurry 34 is pumped through a sealed pipe 48 by pump 49 feeding a remotely located pasteurization vessel 50. The slurry is deposited at the top of the pasteurization vessel to form a bed of chips 35, which is pumped as a slurry from the bottom of the vessel 50 by a pump and discharge device 51, whereby the pasteurization vessel acts as a first-in-first-out ("FIFO") storage container.

The pasteurization vessel 50 maintains the hot slurry so that it is held at or above a predetermined minimum pasteurization temperature T1, the temperature T1 preferably being about 180 degrees Fahrenheit. Preferably, the temperature in the pasteurization vessel 50 is maintained passively, through the use of appropriate insulating material which contains the heat of the slurry. Moreover, the rate at which the slurry 34 is pumped through the pasteurization vessel 50 is controlled so that the time of transit of the slurry through the vessel 50 during which the temperature is at or above the temperature T1 is a predetermined minimum pasteurization time "t", the time "t" preferably being about 75 minutes.

Although only one pasteurization vessel 50 is shown, it is to be recognized that two or more such vessels may be used. In particular, multiple pasteurizing vessels may be used to avoid "rat holing"; that is, to ensure that the slurry flows uniformly through the pasteurization vessel or vessels.

Slurry 34 exiting the pasteurization vessel 50 is pumped downstream by the pump and discharge device 51 to a water separator 52 wherein most of the water is drained off at drain pipe 54. The remaining wet wood chips are placed in a chip pile 56 to await collection and transport.

Preferably, water from the system 10 is reclaimed for recycling through the system. Water drained from the water separator 52 is preferentially sent to a heating system 64 via a stand pipe 58. Any excess water from the drain pipe 54 above what is immediately demanded by the process overflows through pipe 59 into a surge tank 60. Any dearth of water below what is immediately demanded is made up from the surge tank 60.

Recirculated hot water is supplied to the scrubber 38 via inlet 37 and returned via outlet 41 to the stand pipe 58. Drainage and rain water from the chip pile 56 collected on pad 53, which may be made e.g., of concrete or black top, are pumped to the surge tank 60 by pump 61. A fresh water inlet 62 is provided for replacing lost water, primarily as a result of evaporation from and absorption into the wood chips.

The hot water circulation system 28 also employs the heating system 64 for heating the water to a predetermined temperature T2. The temperature T2 is high enough so that, combined with the chips, the resulting temperature of the mixture will be at a predetermined design temperature, e.g., about 188 degrees Fahrenheit. The water may be heated by a hot water heater 70.

The heating system 64 of the hot water circulation system 28 may employ waste heat. The waste heat may be obtained, for example, by a heat exchanger, such as tubular coils 68, coupled to a supplementary heat source 72. In that event, the hot water heater 70 provides heat when sufficient waste heat is not available.

While the waste heat source 72 may be located some distance away, thereby requiring a pump 73, the water heater 70 is preferably located near the water separator 52. The stand pipe 58 is preferably high enough that water will flow by gravity through the water heater 70 and into the hopper 19.

It is to be recognized that, while a specific method and apparatus for pasteurizing wood chips has been shown as preferred, other configurations could be utilized, in addition to configurations already mentioned, without departing from the principles of the invention. In particular, pasteurizing of wood chips may be accomplished without the air circulation system, and by employing other means of providing thereto and subsequently reclaiming therefrom a heated fluid for a predetermined time.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

We claim:

1. A method for preventing the spread of pathogens from comminuted wood delivered in a shipping container in which the comminuted wood is isolated from the local atmosphere to substantially prevent the escape of pathogens therefrom, comprising:

- mixing the comminuted wood with a liquid inside the shipping container to form a slurry for transporting the comminuted wood to a location outside of the shipping container;
- transporting the comminuted wood to the location by flowing said slurry from the inside of the shipping container to the location while said slurry remains isolated from the local atmosphere to substantially prevent the escape of pathogens therefrom; and
- maintaining said slurry at or above a predetermined, elevated temperature for at least a predetermined time at said location while said slurry remains isolated from the local atmosphere to substantially prevent the escape of pathogens therefrom, to pasteurize the comminuted wood.

2. The method of claim 1, wherein said liquid is water, the method further comprising heating said water prior to mixing with the comminuted wood.

3. The method of claim 1, further comprising providing a holding vessel for maintaining said slurry at said predetermined elevated temperature for said time at said location.

4. The method of claim 3, further comprising heating said liquid prior to mixing with the comminuted wood.

5. The method of claim 3, further comprising continuously forming and transporting said slurry to said holding vessel and continuously releasing said slurry from said holding vessel on a first-in-first-out basis to maintain said slurry at or above said predetermined elevated temperature for at least said predetermined time.

6. The method of claim 5, further comprising separating said liquid from said slurry after releasing said slurry from said holding vessel, to recover the comminuted wood.

7. The method of claim 6, further comprising recycling said liquid after releasing said liquid from said slurry to form said slurry.

8. The method of claim 7, further comprising heating said liquid prior to forming said slurry.

9. The method of claim 8, wherein said heating of said liquid is by using waste heat obtained from other independent processes.

10. The method of claim 1, wherein the shipping container has an opening the method further comprising placing a cover over the opening and providing a liquid inlet and a slurry outlet from outside the container to inside the container.

11. The method of claim 10, wherein said cover comprises a housing providing room for machinery and personnel to mix said liquid with the comminuted wood within the container.

12. The method of claim 11, further comprising allowing fresh air into said housing and removing existing air from within said housing, filtering said existing air, and releasing said existing air into the local atmosphere.

13. The method of claim 12, further comprising removing said existing air from said housing at a rate which maintains negative pressure within said housing.

14. A method for pasteurizing comminuted wood, comprising:

- combining a heated fluid with the comminuted wood at a first location to form a slurry;
- pumping said slurry from said first location to a second location;
- maintaining said slurry at said second location at or above a predetermined temperature for at least a predetermined time sufficient to pasteurize the comminuted wood; and
- thereafter separating said heated fluid from said slurry to recover the comminuted wood.

15. The method of claim 14, further comprising recycling said fluid obtained from said step of separating to form said slurry.

16. An apparatus for use in preparing to transport comminuted wood from a sea-going vessel to a receptacle on-shore for pasteurizing the comminuted wood, the sea-going vessel having an opening through an upper decking surface thereof, the opening providing access to a cargo hold disposed beneath the upper decking surface, the opening being covered by a hatch door, the apparatus comprising a housing adapted to be disposed over said opening and said hatch door, and on the upper decking surface of the sea-going vessel, said housing being further adapted so that said hatch door can be fully opened upwardly while said housing is set on the upper decking surface, said housing adapted for sealing with the upper decking surface to substantially prevent the passage of air from the cargo hold to the external atmosphere, wherein said housing is connected to an air outlet for removing existing air from said cargo hold through said air outlet.

17. The apparatus of claim 16, wherein said air outlet is part of an air transfer system which includes a filter in communication with said air outlet.

18. The apparatus of claim 16, wherein said air outlet is part of an air removal and cleaning system which includes a hot scrub in communication with said air outlet for bringing said existing air in contact with a hot liquid.

19. An apparatus for use in preparing to transport comminuted wood from a sea-going vessel to a receptacle on-shore for pasteurizing the comminuted wood to substantially prevent the spread of pathogens to the local atmosphere, the sea-going vessel having an opening through an upper decking surface thereof, the opening providing access to a cargo hold disposed beneath the upper decking surface, the opening being covered by a hatch door, the apparatus comprising a housing adapted to be disposed over said opening and said hatch door, and on the upper decking surface of the sea-going vessel, said housing adapted for sealing with the upper decking surface to substantially prevent the passage of air from the cargo hold to the external atmosphere.

20. The apparatus of claim 19, wherein said housing is connected to an air outlet for removing existing air from said cargo hold through said air outlet.

21. The apparatus of claim 20, wherein said air outlet is part of an air removal and cleaning system which includes a hot scrub in communication with said air outlet for bringing said existing air in contact with a hot liquid.

* * * * *